(12) United States Patent
Kösters

(10) Patent No.: US 9,492,803 B2
(45) Date of Patent: Nov. 15, 2016

(54) PROCESS FOR PERFORMING AN ENDOTHERMIC REACTION

(71) Applicant: SAUDI BASIC INDUSTRIES CORPORATION, Riyadh (SA)

(72) Inventor: Peter Hubertus Kösters, Geleen (NL)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/536,093

(22) Filed: Nov. 7, 2014

(65) Prior Publication Data

US 2015/0064078 A1    Mar. 5, 2015

Related U.S. Application Data

(62) Division of application No. 12/452,362, filed as application No. PCT/EP2008/005265 on Jun. 25, 2008, now Pat. No. 8,916,737.

(30) Foreign Application Priority Data

Jul. 5, 2007  (EP) .................................... 07013192
Nov. 26, 2007  (EP) .................................... 07022847

(51) Int. Cl.
   *B01J 8/06* (2006.01)
   *B01J 19/24* (2006.01)
   (Continued)

(52) U.S. Cl.
   CPC .............. *B01J 8/062* (2013.01); *B01J 19/006* (2013.01); *B01J 19/2415* (2013.01);
   (Continued)

(58) Field of Classification Search
   CPC ...... B01J 8/062; B01J 19/2425; C07C 5/333
   See application file for complete search history.

(56) References Cited

U.S. PATENT DOCUMENTS 2,945,077 A    7/1960  Polk
3,453,087 A    7/1969  Herp, Jr. et al.
(Continued)

FOREIGN PATENT DOCUMENTS

DE    10229661 A1    4/2003
GB    1549736    8/1979
(Continued)

OTHER PUBLICATIONS

Japanese Patent No. 2004002303; Date of Publication: Jan. 8, 2004; Abstract Only, 2 pages.
(Continued)

*Primary Examiner* — Lessanework Seifu
(74) *Attorney, Agent, or Firm* — Cantor Colburn LLP

(57) ABSTRACT

Process for performing an endothermic reaction in a reactor containing catalyst tubes, the catalyst tubes containing a catalyst promoting the endothermic reaction, the process comprising the steps of,
  a. contacting the catalyst contained in the catalyst tubes with a feed flow passing through the channels from an entrance end to an exit end,
  b. contacting an outer surface of the catalyst tubes with a flow of a heating medium having an initial heating temperature and flowing co-currently with the flow of feeds to heat the surface by convection,
  c. mixing at least part of the heating medium after having been contacted with the catalyst tubes with a flow of fresh heating medium having a start temperature higher than the initial heating temperature to form the co-current heating medium having the initial heating temperature and reactor for carrying out the process.

7 Claims, 5 Drawing Sheets

(51) Int. Cl.
*C07C 5/333* (2006.01)
*B01J 19/00* (2006.01)

(52) U.S. Cl.
CPC ......... *B01J 19/2425* (2013.01); *C07C 5/333* (2013.01); *C07C 5/3337* (2013.01); *B01J 2208/00504* (2013.01); *B01J 2219/00763* (2013.01); *B01J 2219/2411* (2013.01); *C07C 2521/04* (2013.01); *C07C 2523/62* (2013.01)

(56) References Cited

U.S. PATENT DOCUMENTS

| | | | |
|---|---|---|---|
| 3,768,980 | A | 10/1973 | Andersen |
| 3,958,951 | A * | 5/1976 | Woebcke ............ C01B 3/384 110/336 |
| 4,769,506 | A | 9/1988 | Kosters |
| 5,073,352 | A | 12/1991 | Dang Vu et al. |
| 5,186,909 | A | 2/1993 | Dang Vu et al. |
| 5,247,907 | A | 9/1993 | Lee et al. |
| 5,350,566 | A | 9/1994 | Stringaro |
| 5,935,531 | A | 8/1999 | Giacobbe |
| 6,191,332 | B1 | 2/2001 | Duee et al. |
| 7,332,139 | B2 | 2/2008 | Schutte et al. |
| 2003/0101651 | A1 | 6/2003 | Weedon |

FOREIGN PATENT DOCUMENTS

| | | | |
|---|---|---|---|
| GB | 2201903 | A | 9/1988 |
| JP | S5863783 | | 4/1983 |
| JP | 59030705 | A | 2/1984 |
| JP | S6339629 | A | 2/1988 |
| JP | 0273888 | A | 3/1990 |
| JP | 2120203 | A | 5/1990 |
| JP | H04190843 | A | 7/1992 |
| JP | 4215836 | | 8/1992 |
| JP | H0634734 | U | 5/1994 |
| JP | H06296854 | A | 10/1994 |
| JP | 07109106H | A | 4/1995 |
| JP | H11179191 | A | 7/1999 |
| JP | 2003336832 | A | 11/2003 |
| JP | 2004002303 | A | 1/2004 |
| JP | 2004167448 | A | 6/2004 |
| JP | 2006097526 | A | 4/2006 |

OTHER PUBLICATIONS

Japanese Patent No. 2006097526; Date of Publication: Apr. 13, 2006; Abstract Only, 2 pages.
Japanese Patent No. H0634734; Date of Publication: May 10, 1994; Abstract Only, 2 pages.
Japanese Patent No. H07109106; Date of Publication: Apr. 25, 1995; Abstract Only, 2 pages.
Japanese Patent No. S6339629; Date of Publication: Feb. 20, 1988; Abstract Only, 2 pages.
Extended European Search Report; European Application No. 07022847.3; Date of Mailing: Sep. 17, 2008; 5 Pages.
German Patent No. 10229661 (A1); Publication Date: Apr. 10, 2003; Abstract Only; 1 Page.
International Search Report; International Application No. PCT/EP2008/005265; International Filing Date: Jun. 25, 2008; Date of Mailing; Sep. 17, 2008; 6 Pages.
Japanese Patent No. 2003336832 (A); Publication Date: Nov. 28, 2003; Abstract Only; 2 Pages.
Japanese Patent No. 2120203 (A); Publication Date: May 8, 1990; Abstract Only; 1 Page.
Japanese Patent No. 59030705 (A); Publication Date: Feb. 18, 1984; Abstract Only; 2 Pages.
Written Opinion of the International Searching Authority; International Application No. PCT/EP2008/005265; International Filing Date: Jun. 25, 2008; Date of Mailing; Sep. 17, 2008; 6 Pages.
Japanese Patent No. 2004167448; Date of Publication: Jun. 17, 2004; Abstract Only, 2 pages.
Japanese Patent No. H04190843; Date of Publication: Jul. 9, 1992; Abstract Only, 2 pages.
Japanese Patent No. H06296854; Date of Publication: Oct. 25, 1994; Abstract Only, 2 pages.
Japanese Patent No. H11179191; Date of Publication: Jul. 6, 1999; Abstract Only, 2 pages.
Japanese Patent No. S5863783; Date of Publication: Apr. 15, 1983; Abstract Only, 2 pages.

* cited by examiner

PROCESS FOR PERFORMING AN ENDOTHERMIC REACTION

CROSS REFERENCE TO RELATED APPLICATIONS

The present application is a divisional of U.S. application Ser. No. 12/452,362, filed Mar. 2, 2010, which is a 371 filing of International Application Ser. No. PCT/EP2008/005265, filed Jun. 25, 2008, which claims priority to European Application No. 07013192.5, filed Jul. 5, 2007, and European Application No. 07022847.3, filed Nov. 26, 2007, all of which are hereby incorporated by reference in their entirety.

The invention relates to a process for performing an endothermic reaction in a reactor containing catalyst tubes, the catalyst tubes containing a catalyst promoting the endothermic reaction.

DE-10229661-A describes a process for the catalytic dehydrogenation of alkanes, which is an example of an endothermic equilibrium reaction. This document discloses a process wherein tubes containing a catalyst are heated by burners positioned between the tubes. By controlling the heat produced by the burners a desired temperature profile along the length of the tubes is said to be imposed for achieving a continuous high selectivity and conversion rate. However, no concrete disclosure is given as to how this should be done in practice. Further, the use of burners in close vicinity of the catalyst tubes causes radiative heating of the tubes which may give rise to hot spots, requiring expensive high-temperature resistant pipe material and causing local coke formation which will necessitate frequent regeneration of the catalyst and may lead to plugging of the tubes. As a further problem associated with local high temperature, further unwanted side reactions can occur.

Aim of the present invention is to provide a process for performing an endothermic equilibrium reaction that causes a favourable temperature profile along the reaction tubes, avoiding local hot spots.

This aim is achieved according to the invention in that the process comprises the steps of contacting the catalyst contained in the catalyst tubes with a feed flow passing through the channels from an entrance end to an exit end, contacting an outer surface of the catalyst tubes with a flow of a heating medium having an initial heating temperature and flowing co-currently with the flow of feeds to heat the surface by convection, mixing at least part of the heating medium after having been contacted with the catalyst tubes with a flow of fresh heating medium having a start temperature higher than the initial heating temperature to form the co-current heating medium having the initial heating temperature.

By using convective heating of the tubes in combination with partial recirculation of the heating medium an initial heating temperature can be guaranteed that is below a maximum level so that common and less expensive materials as stainless steel can be used for the tubes. The present process allows controlling the flow rate and initial heating temperature of the heating medium independently, so the temperature profile along the tubes can be controlled very accurately. Further said flow rate and initial heating temperature in combination with the tube dimensions can be chosen such that an optimal axial temperature profile along the tubes can be achieved.

The catalyst contained in the catalyst tubes is contacted with a feed flow passing through the tubes from an entrance end to an exit end. Travelling through the tubes the feed will be converted into the desired product.

Preferably the feed flow is subjected to a critical pressure drop at the entrance end of each tube. This avoids different flow rates of the feed through different tubes. Lower flow rates in some tubes will lead to higher temperatures in those tubes, potentially up to unwanted high temperatures causing catalyst degradation and unwanted side reactions in those tubes. Coke formation is one of these undesired side reactions and will further decrease the flow rate and finally lead to plugging of that tube.

Catalysts applicable in the process according to the invention essentially are particulate catalysts, which preferably are present as a fixed bed in the tubes.

In the following it will be assumed that the reactor tubes run vertically and the co-current streams of feeds and heating medium run in upward direction from the lower part, denoted as bottom or inlet, to the higher, top or outlet, part of the tubes. It is also possible to carry out the process of the invention with said streams running co-current in a downward direction or to apply a reactor in which the tubes run horizontally or at an angle with the horizontal plane.

The initial heating temperature of the heating medium is considerably higher than the temperature of the feed entering the catalyst tubes. The enthalpy of the heating medium will be sufficient to compensate the heat consumed by the endothermic reaction of the feed and to heat up the feed/product mixture in the tubes. The temperature difference between the heating medium and the contents of the tubes is the driving force for this heat exchange. This difference will decrease along the tubes from inlet to outlet and so the rate of heat transfer will decrease from inlet to outlet. Since the remaining amount of unconverted feed will also decrease from inlet to outlet also less compensating heat is required. Preferably the flow rate and initial temperature of the heating medium are chosen such that the temperature of the tube contents will not decrease along the tube from bottom to top and more preferably they are chosen such that said temperature continuously increases along the tubes. The flow rate and initial temperature of the heating medium will be chosen such that the temperature of the tube walls and tube contents at their outlet end remains below a temperature where feed or product decomposition, coke formation and other unwanted side reactions may occur.

In the process according to the invention the reaction at the entrance of the tubes will run at a high rate due to the presence of the highest amount of unconverted feed. The high initial temperature of the heating medium will compensate for the heat consumed and even raise the temperature of the tube contents. Due to the continuous further heating along the length of the tube the reaction closely follows the increasing equilibrium conversion, resulting in high conversion of the feed at the exit end. The highest temperature the catalyst can withstand in fact is the main limiting factor in reaching full conversion. In the present process the main part of the feed is already converted at relatively low temperature and the selectivity of the reaction has appeared to be high.

Also with a proper choice of initial heating temperature and flow rate a situation can be achieved in which the temperature of the tube walls is nearly constant over the largest part of their length.

Preferably the feeds are preheated to a minimum temperature necessary for the catalyst to be active before contacting them with the catalyst. This temperature causes the reaction to start running already at a high rate at the inlet end, the rate being driven by the distance to the equilibrium at the governing temperature and with less risk of unwanted side reactions than at higher inlet temperature. Moving upwards, the temperature of the feed, gradually mixed with an increasing amount of product formed, and of the catalyst will increase by heat exchange with the heating medium and this raise of temperature favours the reaction rate, even to such extent that the reaction was found to follow the increasing equilibrium conversion by increasing temperature, giving an optimal overall conversion.

It was found that the conversion efficiency of the process can be even enhanced when the catalyst tubes from bottom to top are filled with layers of at least two different catalysts, wherein the catalyst closest to the bottom is selected for its relatively high activity while a relatively lower temperature resistance or a relatively low level of another temperature-dependent catalyst property may be accepted, and the catalyst closest to the top is selected for its relatively high temperature resistance or a relatively high level of another temperature-dependent catalyst property while a relatively lower activity may be accepted. If more than two catalyst layers are used, temperature resistance or the level of another temperature-dependent catalyst property of the layers will increase from bottom to top, if inevitable accepting some decreases in their activity from bottom to top. This allows optimal use of the controlled temperature profile along the tubes, obtaining the highest possible conversion and possibly also selectivity. Relatively is used here with respect to adjacent layers.

The controlled temperature range over the tubes allows applying heat sensitive catalysts in the process according to the invention. Overall the process according to the invention safeguards high catalytic activity for a long time.

To improve conversion selectivity and catalyst life cycle the feed stream may be diluted with an inert gas, e.g. with carbon dioxide, nitrogen or steam, steam being preferred. If diluted the dilution ratio will depend on the reaction carried out in the tubes and in practice will range from 0.1 or 2 to 12 moles inert gas per mol feed.

It is also possible to add 0.01 to 1 mole $H_2$ per mole per mole feed instead of an inert gas, e.g. when the catalyst used is not compatible with the inert gases.

The heating medium, flowing along the tubes will transfer heat to the walls of the tubes, which in turn transfer the heat to the catalyst and the feed. When this heating medium stream reaches the top of the tubes it will have been cooled down from the initial heating temperature to a lower temperature. As described later, part of the heat energy still present in the medium can be used to generate steam or for other process heat integration purposes, which will cool down the medium even further. At least part of the cooled medium will be recirculated for controlling the initial heating temperature of the heating medium. This can be done by mixing freshly generated heating medium, e.g. flue gas of a burner or fresh steam. This fresh medium will generally have a higher temperature than the initial heating temperature. By mixing it with a controlled amount of the heating medium, that has been cooled by having been contacted with the catalyst tubes, and optionally also by a further heat exchange e.g. for generating steam, fresh co-current heat medium is formed having the desired initial heating temperature.

Another way to achieve the desired initial heating temperature, applicable when the fresh heating medium is to be generated by a burner, is applying the recirculated cooled heating medium through the burner to mix it with the flue gas immediately when it is generated by the combustion.

The fresh heating medium can be steam but preferably the fresh heating medium consists of flue gases from a burner, e.g. a gas or oil burner. The amount of flue gases produced by such burner can easily be controlled, which allows versatility in the ratio fresh heating medium to recirculated cooled heating medium in order to obtain heating medium with the desired initial heating temperature and flow rate for bringing into contact with the catalyst tubes again.

The process according to the invention allows keeping the temperature along the whole length of the tubes between a maximum temperature where catalyst degradation, unwanted side reactions may occur and a minimum temperature required for the reaction to run at an acceptable rate.

In the process according to the invention the amount of hot gases from the burner and the amount of colder recirculated spent heating medium can be independently controlled. This causes great versatility in both the flow rate and the initial temperature of the heating medium independently, allowing controlling the heat exchange profile along the length of the catalyst tubes over a broad range. In the known process the ratio between fuel gas and combustion air is the only control parameter. This allows only limited variation in flow rate and temperature since variation in the amount of air is restricted by the minimum amount of oxygen required for burning the fuel gas.

In the process according to the invention no radiative heating of the catalyst tubes by the burner will be allowed by proper positioning the burners relative to the catalyst tubes, positioning screens between the burner flames and the catalyst tubes, insulating the catalyst tubes on spots exposed to radiation or combinations of these measures. The heating of the catalyst tubes occurs then through convective heating only.

The tubes in the reactor can be conventional reformer pipes as known from DE-A-10229661. Such pipes can be applied as catalyst tubes in the process according to the invention, avoiding the radiative heating and its associated problems. However, they have a serious trade-off in catalyst volume and heat transfer properties. To avoid unwanted radial temperature gradients their diameter should be relatively small. This will require a large number of pipes to obtain a desired catalyst volume. Also catalyst replacement is a tedious process.

These and other problems associated with the known tubular reactors were found to be solved in a preferred embodiment of the process according to the invention by applying a panel reactor as described below.

The process according to the invention is suitable for performing endothermic reactions. Examples of this type of reaction that can be performed with favourable results with this process include endothermic equilibrium reactions for example dehydrogenations of $C_2$-$C_8$ alkanes to olefins (e.g. ethylene, propylene and isobutylene), dehydrogenations of mixtures of $C_2$-$C_8$ alkanes and olefins to diolefins (e.g. butadiene and isoprene), dehydrogenation of ethyle benzene to styrene and non-oxidative dehydrogenations of alcoholes to aldehydes (e.g. methanol to formaldehyde and ethanol to acetaldehyde) and dehydratations of $C_2$ to $C_8$ carboxylic acids to their intra-molecular anhydrides, and irreversible reactions for example catalytic cracking of higher olefins to lower olefins.

A reaction that has proven to be very suitable for being performed with the process according to the invention is the dehydrogenation reaction of a hydrocarbon, with one or more saturated carbon bonds, in particular a $C_2$-$C_8$ alkane like ethane, propane, (iso) butane, (iso) pentane, hexane, heptane, and octane, and ethyl benzene. These reactions run with higher conversion at high reaction temperatures. The allowable maximum reaction temperature is limited by the catalyst that may decompose or lose its activity at high temperature. In practice temperatures of about 500 to 750° C. are applied and thus will benefit most from continuous heat supply by the heating medium along the whole length of the reaction tubes. Higher temperatures can be used when the available catalysts allows so.

Carrying out the process according to the invention imposes specific requirements to the reactor. Thus the invention further relates to a reactor for performing an endothermic equilibrium reaction process, comprising a heat providing section containing heat providing means, the heat providing section communicating with an inlet end of a reactor section, the reactor section containing catalyst tubes and having an outlet end communicating with a head space section, the catalyst tubes being screened from heat radiation by the heat generating means, the reactor further comprising a recirculation section connecting the head space section to the heat providing section.

The reactor comprises a heat providing section. In this section the heating medium flow for supplying the required heat to the catalyst tubes is prepared. The heat providing means may comprise one or more burners, for generating flue gas. These means also may be an inlet for steam of proper temperature. Further this section contains as connection to the recirculation section an inlet for recirculated spent heating medium.

The recirculated heating medium inlet can be connected with the heat providing section at a position downstream from the burner or steam inlet. It can also be connected so close to the burner that it mixes immediately with fresh flue gas.

The heat providing section communicates with an inlet end of a downstream reactor section. Communicating here means that there is a connection open for the heating medium stream. At the same time the catalyst tubes are screened from radiative heating by the heat generating means. Radiative heating of the catalyst tubes may cause local hotspots which are to be avoided. To achieve this screening there may be provided an optically closed pathway from burner flames to catalyst tubes. To this end the heat providing section and the reactor section may be positioned under a certain angle, preferably by a 90° bend, or baffles may be present between heat providing and reactor section, leaving a path way for the heating medium but blocking any straight optical path way to the catalyst tube for radiation from the burners. Another way to avoid radiative heating of the catalyst tubes is thermally insulating those parts of the catalyst tubes that face the burner flames.

The reactor further comprises a reaction section. This reaction section contains reactor tubes to be filled with catalyst particles that can promote the endothermic reaction to be conducted in the reactor. The reactor tubes generally run parallel to a length axis of the reactor and in general also in a substantially vertical direction.

A known concept for such reactor tubes is the known multi-tubular reactor, comprising a bundle of parallel pipes. Each pipe is individually connected to a feed line providing the feed stream resp. a product line for removing the formed product from the reactor for further processing.

The reaction section may further comprise means to create a desired flow pattern of the heating medium along the catalyst tubes, e.g. in the form of baffles.

The reactor according the invention has an inlet end, connected to and communicating with the heat generating section, through which the heating medium can enter the reaction section for heating the catalyst tubes. The reactor section also has an outlet end positioned opposite to the inlet end beyond and upstream the catalyst tubes connecting the reactor section to a head space section.

The head space section is designed for collecting the spent heating medium, i.e. the heating medium after it has passed and left the reactor section. It may contain heat exchange equipment for further distracting heat from the spent heating medium, e.g. for generating steam or for pre-heating feed.

The head space section has at least one connection to a recirculation section. This recirculation section connects the head space section to the heat providing section. It may comprise means to control the amount and temperature of spent heating medium to be supplied to an inlet of the heating section.

The head space section may further comprise an outlet for spent heating medium that is not recirculated to the heating section of the reactor. This outlet can be connected to equipment for further gaining heat energy still remaining in the spent heating medium.

Preferably the heat providing means are at least one burner. The temperature of the flue gas heating medium is controlled then by either mixing the flue gas with the cooler recirculated spent heating medium or by feeding the recirculated spent heating medium in such close vicinity of the burner flame that the generated flue gas will be diluted and cooled immediately. In the last case also the NOx content of the flue gas heating medium may be reduced.

The ratio of recirculated heating medium to fresh flue gas will be chosen to obtain heating medium having the desired temperature and flow rate. In practice ratios from 90%-10% to 10%-90% will be applied.

The reactor will further comprise means for distributing the feed to the catalyst tubes and for collecting the formed product from the tubes. It may also comprise means for evenly distributing the heating medium over the reactor tubes to avoid local hot or cold regions in the reactor.

The reactor will also comprise means to supply a feed stream to the reaction tubes, connected to an external feed line and means to convey a mixed feed-formed product stream from the reaction tubes, connected to a product line.

In a preferred embodiment product line and feed line are connected to a heat exchanger for heat exchange between the feed stream and the higher temperature product stream. This construction has the advantage that the temperature of the feed stream will remain in a safe range avoiding coke forming and other unwanted side reactions.

Preferably the reactor according to the invention comprises reactor panels that comprise channels that function as catalyst tubes.

In this case the reactor further comprises a feed line and a product line and the reactor section contains reactor panels, each reactor panel comprising a feed header, a product header and adjacent channels, each channel having a length, running from an entrance end to an exit end, and wherein the entrance ends are directly connected to and open into the feed header and the exit ends are directly connected to and open into the product header and wherein the feed header has at least one connection to a feed line and the product header has at least one connection to a product line and wherein part of at least one of the feed header and the product header is detachable giving access to the channel ends.

The panels in the reactor will be positioned between the inlet end and the outlet end of the reaction section of the reactor and can be separately and easily exchanged and the panels allow great versatility in dimensions and give great flexibility in applying heating media to obtain desired temperature profiles along the catalyst tubes.

Instead of a bundle of single pipe as in the known multi-tubular reactor the required reaction volume can be built up from a number of reactor panels, each having one feed entrance and one feed exit for a number of channels rather than for each single pipe and being easier for handling, maintaining and replacing catalyst. Increasing reaction volume does not require connecting more and more single tubes to the feed and product lines, but can be simply achieved by adding more or other type panels.

The reactor channels are mutually connected. Thus they form a unity having high stiffness against bending allowing a panel to be hung into the reactor, only supported at a top end.

The entrance ends of the channels directly connect to and directly open into the feed header which is to be understood that there is an open connection through which reactants from the feed header can enter into the channels, the entrance end of the channel being visible from within the header. Directly thus is to be understood as containing no intermediate construction elements as pig tails, bellows, pipes and the like but only direct connecting means like bolted flanges and welds.

Preferably the entrance end of each catalyst tube is provided with flow restricting means suitable to impose a near-critical pressure drop on a feed flow entering the tube. This secures a constant feed flow rate to the channels, even when the channels do not have exactly the same pressure drop. Difference in pressure drop may occur due to differences in catalyst filling or packing within considerable ranges and also may occur during operation by coke build up. The near-critical pressured drop is defined as the pressure drop causing the flow velocity to be at least 50%, preferably at least 70, more preferably at least 80% of the critical flow velocity.

The reactor further may contain shielding means to avoid direct exposure of the panels to the reactor walls that may cause temperature differences between the panels closest to the walls and the other panels. These shielding means then can be temperature controlled separately from the other panels. An example of such shielding means are panels as those containing the catalyst but not containing catalyst and being cooled internally.

Further details, specifications, alternative and preferred embodiments and advantages of the panels as means to provide the catalyst channels are disclosed in the publication based on the priority document of the co pending EP application number 07013192.5, the contents of which are incorporated herein by reference.

At least one of the feed header and the product header is detachable as a whole or partly giving access to the channel ends.

A partly detachable header may comprise an opening locked by a detachable part. The part may be hinged to a header edge that can be brought into an open position or may be a loose part that can be connected to and taken off the opening. The part must be gas and liquid tight connectable to the header and preferably also be easily removable. The connection may be established by bolting the detachable part to the header but the part may also be welded to the header and ground along the weld line for detaching the part.

After detaching the detachable part, the opening is giving access to the channels ends. This allows easy emptying, cleaning and refilling of the channels. Preferably such opening is present both in the feed and the products header. This allows emptying the channels through one header, positioning the panel such that this header is in a lower position than the other header and refilling the channels from above through the other header, keeping the panels in the same position.

The opening can be present in a header wall facing the ends of the channels or in a wall normal to the length direction of the channels. The former embodiment of these two is preferred as giving the easiest access.

The channels preferably are arranged in at most two rows, each row defining a flat or curved plane, the planes running substantially parallel. Thus the panels remain slim in a first dimension and provide a large area for heat exchange relative to their volume. Preferably the channels are arranged in one straight or bent row to adapt to the shape of the reactor housing the panels are to be placed into. The feed and product headers then follow the shape of the channel row. Thus the panels are flat and when arranged in parallel at a proper distance in the reactor the channels can be easily accessed by a heating medium flowing in the space between the panels, allowing accurate temperature control of the channels over their lengths.

The panel can be constructed simply and cheap e.g. from basic elements like tubes, folded plates, fittings, sheets and commonly known construction techniques as welding, bolt joints and others.

Preferably the reactor according to the invention containing reactor panels, the reactor panel is composed of a first and a second parallel plate, bordered by a first pair of substantially parallel outer edges and a second pair of outer edges connecting the edges of the first pair, wherein at least the first plate comprises alternating flat connection strips and channel recesses having an entrance end and an exit end, the strips and recesses running normal to the first pair of edges, wherein the plates are joint together at least along the second pair of outer edges and the connection strips, combining the channel recesses of the first plate and the facing part of the second plate into channels, the panel further comprising a feed header, a product header and adjacent channels, each channel having a length, running from an entrance end to an exit end, and wherein the entrance ends are directly connected to and open into the feed header and the exit ends are directly connected to and open into the product header and wherein the feed header has at least one connection to a feed line and the product header has at least one connection to a product line and wherein part of at least one of the feed header and the product header is detachable giving access to the channel ends The channels are present as a combination of a channel recess of one plate and the opposite part of the other plate. This part may be a channel recess, a flat strip or another flat part of that other plate.

The channels are intended to be filled with catalyst particles in such a way that empty spaces that run along the whole length of the channel are avoided as much as possible. Thus fluid entering the channels at the entrance end is prevented from reaching the exit end without having been sufficiently in contact with the catalyst and remaining unreacted. Although the cross section of the channels may have any shape, for the above reason the cross section of the channels preferably have a smooth and regular shape without sharp angles. Examples of such shapes are circular, elliptical or polygonal shapes with rounded edges.

The construction elements forming the panels should consist of materials matching the reaction and process conditions and components that they will be exposed to. Known materials for use under chemical reaction conditions are metal, metal alloys and ceramic materials. It is also known in the art to apply protective coating layers. The skilled person will be able to select the proper materials in view of the intended use. Preferably the material shows sufficient heat conductivity.

The dimensions of the panels are mainly determined by the length and the number of the channels. These values may range broadly, depending on the type of reaction, the production capacity, the size and type of catalyst it is intended for. Since a large advantage of the panel is its modular character each panel may be of considerably smaller size than a single multi-tubular pipe bundle needed in a reactor for the same reaction and having the same production capacity as a corresponding multitude of panels.

Cross sectional area of the channels will depend on the type of catalyst and reaction. The more endothermic the reaction runs the smaller this area will have to be to avoid an inhomogeneous reaction profile, in particular large radial temperature gradients, in the catalyst bed and to secure sufficient heat transport from the catalyst bed to or from the channel walls. In practice said area will lie between 5 and 300 $cm^2$. Preferably the area is less than 200, 100 or even 50 $cm^2$.

More critical than the area of the channels is the smallest linear dimension of a cross section of the channels. Preferably the shortest linear distance from any point of the channel cross sectional area to the channel wall is at most 3.5 cm. More preferably this distance is at most 2.5 cm. Shape of the channels may be circular, ellipsoidal or other smooth and regular shapes without sharp edges.

Channels must not have a too flattened shape in order to allow the desired flow within it. To this end, as a practical rule, the longest of all shortest linear distances should preferably be at least 1 cm when a solid catalyst is used and at least 2 mm when a gaseous catalyst is used.

The length of the channels may vary within wide boundaries, the upper length potentially being restricted by the pressure drop over the length of the channel. This pressure drop may also depend on the type and density of the catalyst bed. Suitable lengths will range from 0.5 to 10 meters.

The wall thickness of the channels, this thickness being the thickness of the plates in case the panel is constructed from two parallel plates, will be sufficient to withstand mechanical forces exerted on it, e.g. by pressure differences, gravity or mounting activities. At the upper limit the thickness will be practically limited for panels according to the invention composed of two parallel plates by the requirement that the plates can be shaped by usual techniques. Practical thickness may range from 0.5 to 5 mm.

Correspondingly the dimension of the panel will be determined by the sum of the dimensions of the composing parts. As an example, this dimension in the direction of the length of the channels will be at least equal to the length of the channels plus the height of the feed and product header in that direction. Also the thickness of the panel being its dimension normal to the direction of the length of the channels will be at least equal to the diameter of the channel in that direction plus the wall thickness of the channel and the thickness of any sheets on the outer surface.

This panel can be constructed easily and with high versatility by known techniques e.g. for manufacturing central heating radiator panels or in automotive industry. Forming metal plates into desired shape and profile by e.g. hot pressing allows to produces plates having complex shape and profile patterns. In another suitable process for constructing this panel, known as cold hydraulic pressing, two flat plates are welded together at the position of the edges and all other positions where the plates should be connected in the panel to be shaped and applying hydraulic pressure between the two plates in order to inflate the non-welded parts into the required channels and headers.

Further details, specifications, alternative and preferred embodiments and advantages of these panels as means to provide the catalyst channels are also disclosed in the publication based on the priority document of the co pending application EP application number 07013192.5,the contents of which are incorporated herein by reference.

Also the reactor according to the invention offers great versatility with respect to heat exchange properties. The relative position and distance of the panels can be freely chosen allowing creating envisaged and effective heat exchange flow between panels and heating medium. Thus the reactor according to the invention has the advantage that no baffles are required to create a desired heating medium flow pattern in the reaction section along the panels. As a further advantage of the reactor according to the invention, in case of plugging of channels, leakage or other incidents only the panel involved has to be removed from the reactor and replaced or just cut off before production can be resumed. Repair or catalyst replacement can be done per panel off-line while production is continued. In the known reactor comprising a single tube bundle production is shut down until repair or catalyst replacement is finished.

In order to allow easy removal of panels, the part of the reactor above the reaction section preferably is, at least partly, detachable.

Preferably the connection from the panel to the feed line is flexible in the sense that differences in thermal expansion between the panels and the connection to the feed line can be absorbed minimizing stresses. Constructive elements to achieve this flexibility are known in the art and as examples can be mentioned that the feed line contains a pigtail tube part or a bellow shaped connection part.

The panels usually will be vertically positioned in the reactor. The channels then run substantially vertically and the headers will run essentially horizontally. The panels usually will be arranged in parallel at a distance of each other. This distance may depend on the heating medium flow regime envisaged for the required heat transfer and may range between 1 mm and 3 cm. Larger distances are possible but have proven less efficient for heat exchange and also require a larger heating medium flow. The distance between the panels meant here is the shortest normal distance between two adjacent parallel panels, measured between the channel of one panel to the opposite part, channel or strip, of the adjacent panel.

The panels can be mounted within the reactor supported by but not fixed to constructive elements of the reactor housing. The housing of the reactor is the total of constructive element shielding the inner reactor volume from the environment and will have the normal and known properties of a reactor housing adapted to match with the governing reaction and heat exchange conditions. In particular the housing comprises at least the heat generating section, the reactor section and the head space section.

Preferably the panels can move with respect to the housing when shrinking or expanding. This avoids the occurrence of thermal stresses between the panels and the housing.

Preferably the panels are hung only supported at their higher end. This allows thermal expansion or shrinkage of the panels only causing minimal stresses stretching the operational life and reliability of the panels and thus of the reactor as a whole.

The invention further relates to the use of the reactor according to the invention for conducting the process according the invention.

In particular the invention relates to the use of the reactor according to the invention comprising reactor panels of the described construction for the dehydrogenation reaction of a saturated hydrocarbon or ethyl benzene, in particular of C2-C8 alkanes.

The invention will be further elucidated by the following drawings. In these drawings FIG. 1 is a cross section of a first embodiment of the reactor according to the invention containing pipes as reactor tubes;

Figure 1:
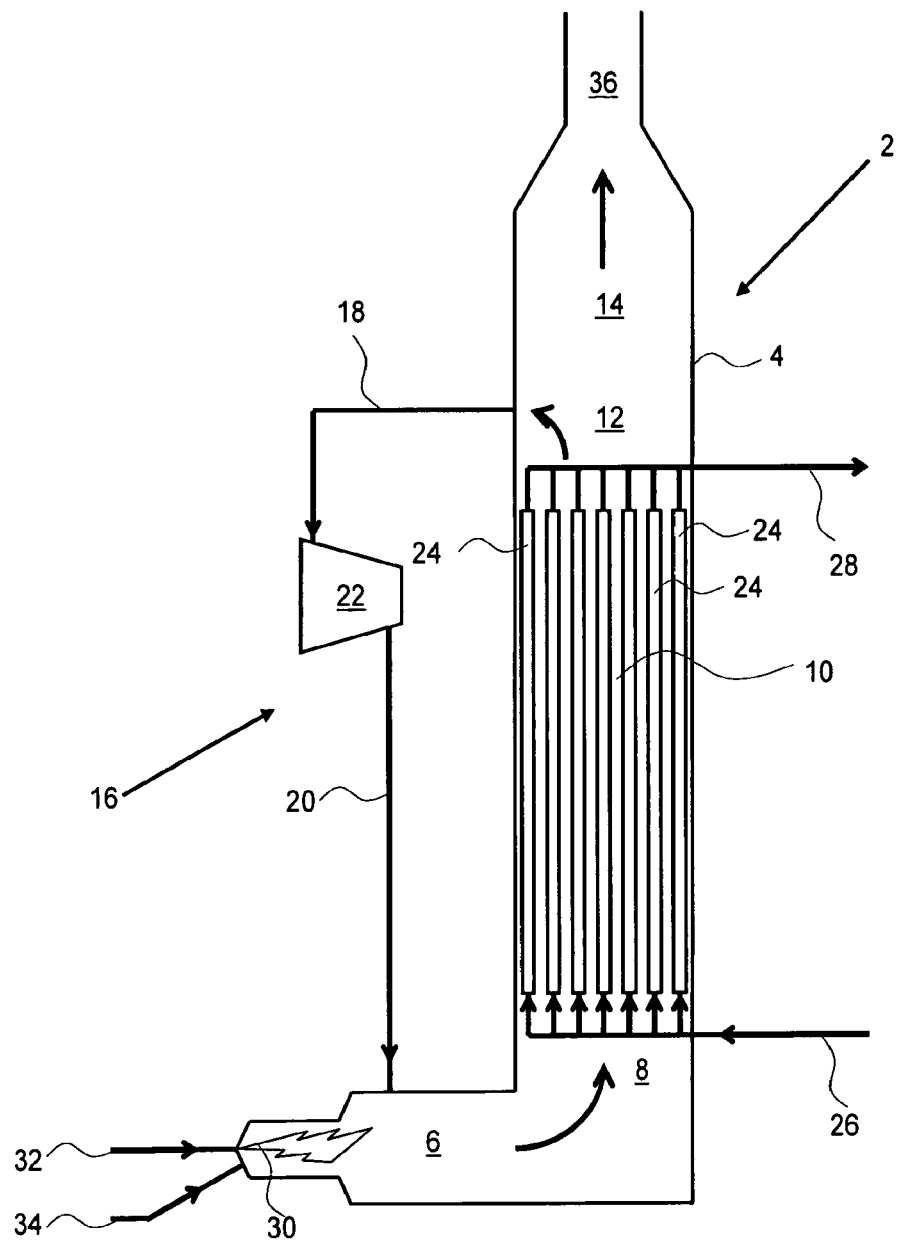
Figure 2:
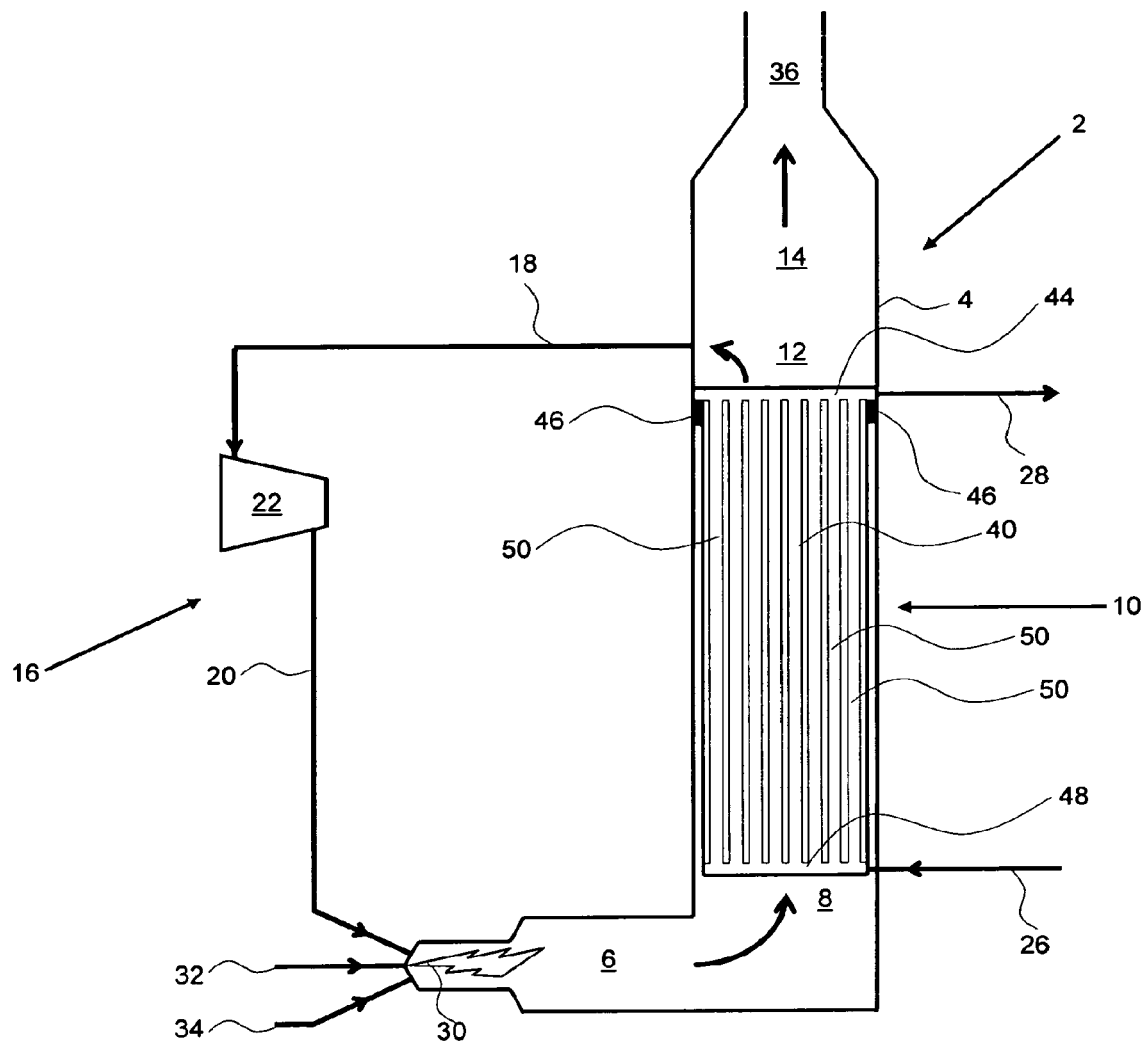
FIG. 2 is a cross section of a second embodiment of the reactor according to the invention containing reactor panels.
Figure 3:
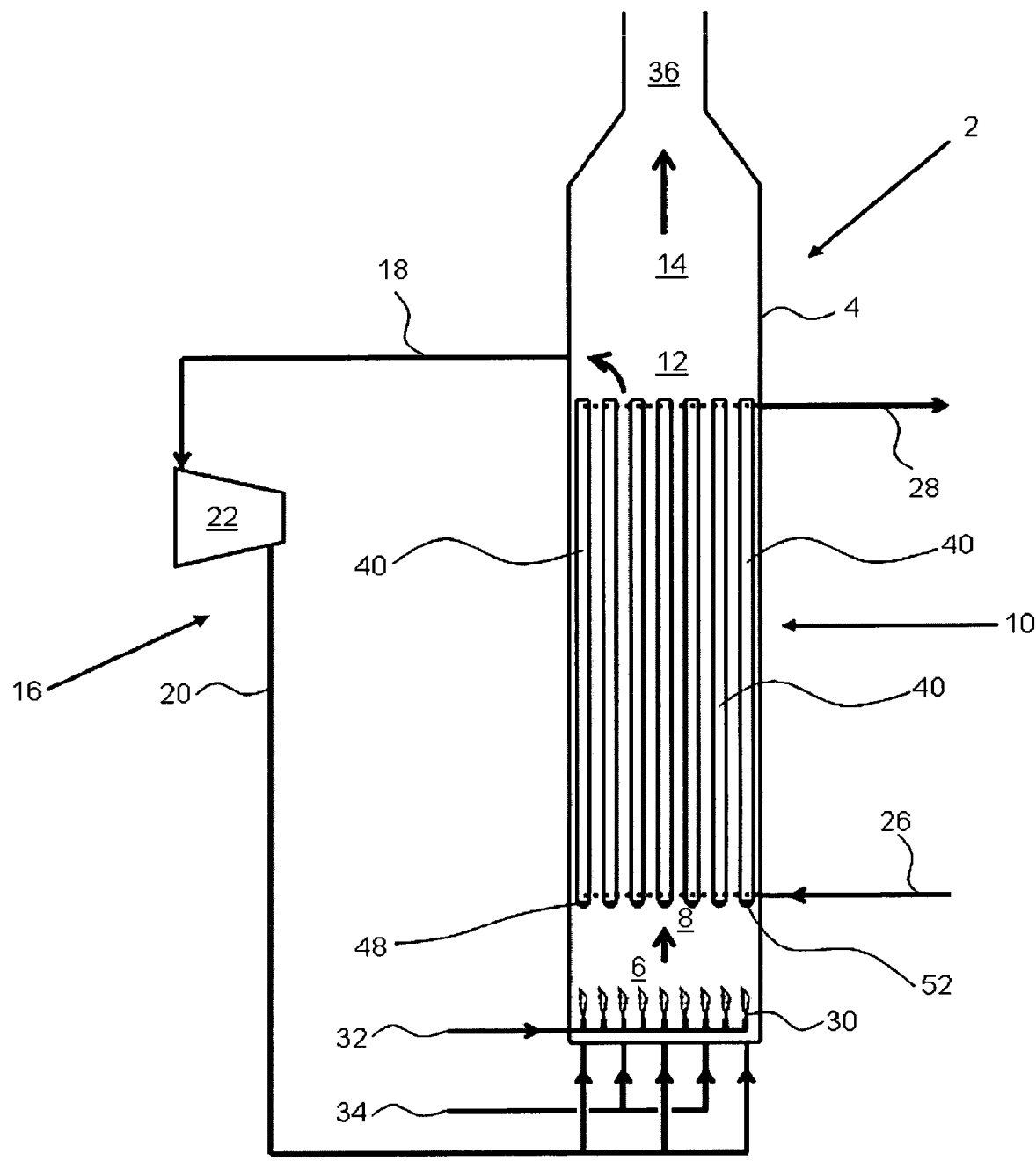
FIG. 3 is a cross section of a third embodiment of the reactor according to the invention containing reactor panels.

In FIGS. 1, 2 and 3 is a reactor having reactor wall 4. The reactor comprises heat providing section 6, inlet end 8 to reaction section 10, outlet end 12 from reaction section 10, head space section 14 and recirculation section 16, comprising of ducts 18 and 20 and compressor 22.

In FIG. 1 reaction section 10 contains reactor tubes 24, at the inlet end of the reaction section connected to feed line 26 and at their opposite end to product line 28.

In FIGS. 1,2 and 3 heat providing section 6 is positioned under an angle of 90° with respect to reaction section 10. This construction screens the reactor tubes from heat radiation generated by heat generating means 30. Heat generating means 30 in this embodiment is a burner connected to a fuel inlet 32 and a combustion air inlet 34.

Head space section 14 is connected to used heating medium outlet 36 which leads to an external heat recovery section (not shown). It is also connected to duct 18 of recirculation section 16, which in turn is connected to compressor 22. The outlet of compressor 22 is connected by duct 20 to heat generating section 6, where recirculated medium will be mixed with produced fresh heating medium.

In FIG. 2 item 40 is a reactor panel, seen from a front side, that is freely hanging in the reaction section 10 with its product header 44 resting on support protrusions 46, fixed to reactor wall 4. Feed header 48 is connected to feed line 26 and product header 44 is connected to product line 28. Panel 40 comprises catalyst channels 50.

Duct 20 is entering heat generating section 6 through the bottom of burner 30 allowing mixing of the recirculated used heating medium with the fresh heating medium immediately when the latter is generated. Numbers not mentioned specifically have the same meaning as in FIG. 1.

In FIG. 3 heat generating section 6 is positioned vertically below the reaction section 10. In reaction section 10 a number of reactor panels 40 is positioned, seen from aside. Bottom part of feed headers 48 of reactor panels 40 are coated with layers 52 of heat insulating material for screening the parts of the panels facing burner 30 from heat radiation of that burner 30, here an array of small burners.

Numbers not mentioned specifically have the same meaning as in FIG. 1.

Figure 4:
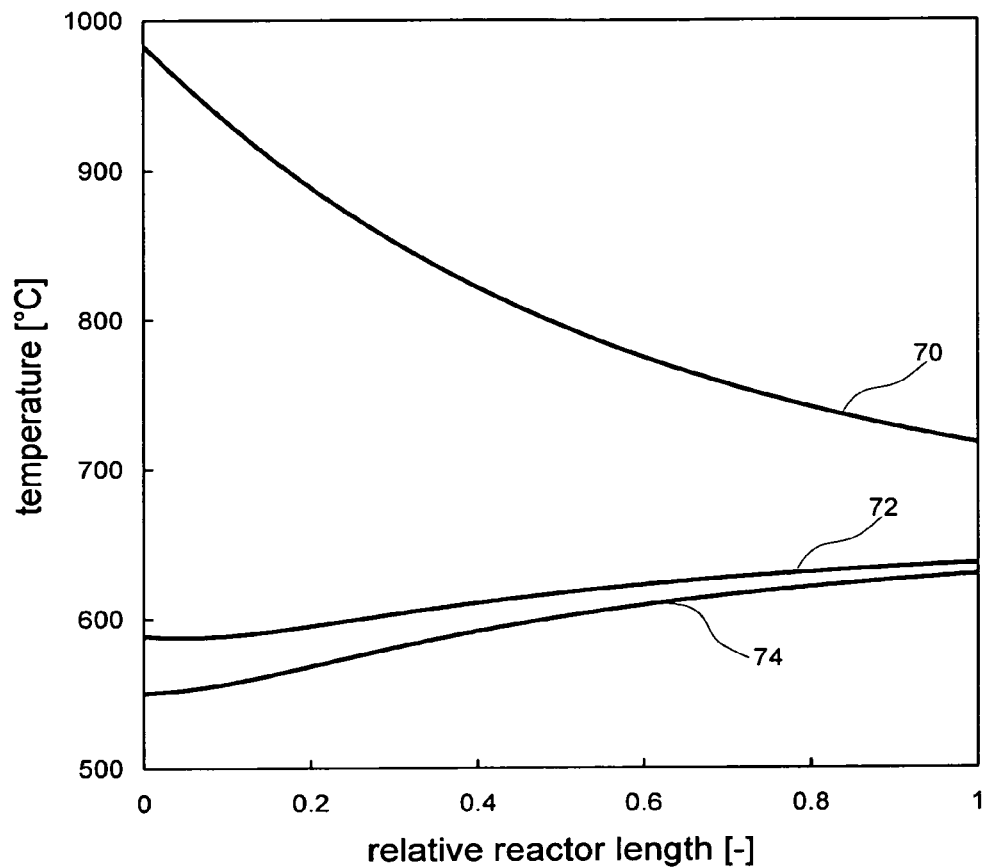
FIG. 4 is a graph showing temperature profiles of heating medium, wall and feed/product stream along the length of the reactor.

FIG. 4, in which the X-axis denotes the relative reactor length from inlet end (0) to outlet end (1) and the Y-axis denotes the temperature in ° C., shows three temperature profiles from inlet end to outlet end of the reaction zone in a reactor as described in FIG. 3 wherein the catalyzed dehydrogenation reaction of propane to propylene is conducted under the conditions as described in Example 1.

Line 70 shows the temperature profile of the heating medium as it flows from the inlet side of the reaction section to the outlet side thereof, gradually cooling down as it transfers heat to the catalyst channels. Line 72 shows the corresponding temperature profile for the wall of the catalyst channels that absorb heat from the heating medium flowing along them. The curve 72 shows the temperature rise resulting from the absorption of heat from the heating medium and the transfer of heat to the feed/product stream in the catalyst tubes. Line 74 shows the corresponding temperature profile for the feed/tube contents themselves, resulting from heat transferred by the wall of the catalyst channels and the heat consumed by the endothermic reaction in the catalyst channels.

The wall temperature shows a very moderate variation over the tube length which prevents thermal and mechanical stress in the reactor construction and prevents local hot spots.

Figure 5:
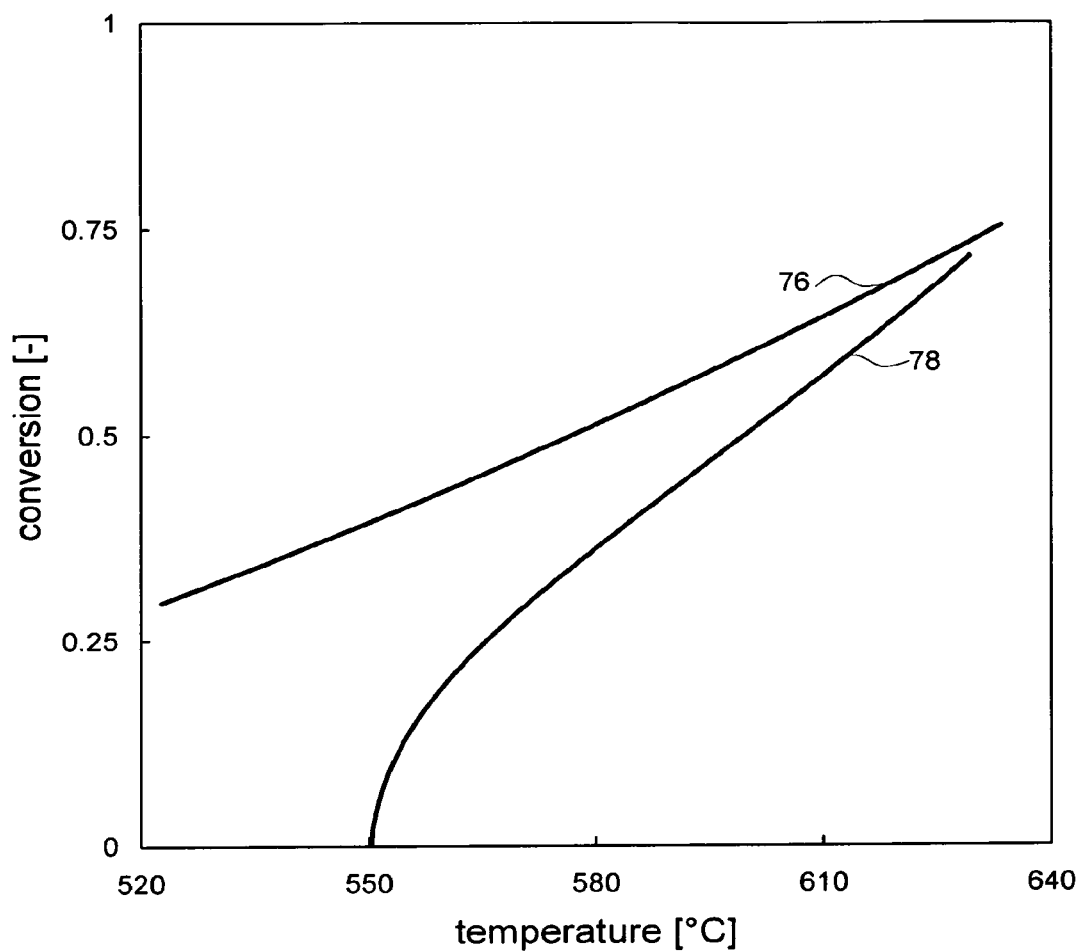
FIG. 5 is a graph showing the equilibrium conversion line and actual conversion line in a catalyst tube in the reactor according to the invention.

In FIG. 5, in which the X-axis denotes the temperature in ° C. and the Y-axis denotes the conversion, line 76 is the equilibrium conversion line of the dehydrogenation reaction of propane to propylene. Line 78 shows the actual conversion along the length of the catalyst channels from inlet end to outlet end of the reaction section as a function of the increasing feed/conversion stream temperature (cf. line 74 of FIG. 4). In the first quarter of the temperature range the conversion is mainly driven by the large amount of unconverted feed present, in the last quarter the higher temperature is the main driving force. As a total result nearly the equilibrium conversion at the highest temperature is achieved. The maximum conversion is restricted by the maximum allowable temperature in view of catalyst degeneration or the occurrence of unwanted side reactions.

The invention will be elucidated by the following examples, without being restricted thereto.

Example I

Propane Dehydrogenation

In a reactor as shown in FIG. 3, wherein the catalyst channels of the reactor panels is filled with a Pt/Sn on alumina carrier as catalyst, propane is dehydrogenated to propylene.

A mixture of steam and propane (steam-to-propane ratio of 3.5 mole/mole) having a temperature of 550° C. and a pressure of 0.25 MPa is supplied to the feed headers of the reactor panels at LHSV of 1.5 $m^3propane/m^3cat.h$. After passing through the catalyst tubes the effluent feed/product mixture has a temperature of 630 degrees and a pressure of 0.15 MPa. Heating medium is supplied to the inlet end of the reaction section with a temperature of 1000° C. After passing the reaction section the used heating medium has a temperature of 715° C.

The wall temperature of the catalyst channels at the inlet end is 565° C., at the outlet end 635° C.

The propane conversion amounts 72% and selectivity towards propylene amount 89%.

The invention claimed is:

1. A reactor for performing an endothermic reaction process, comprising a heat providing section containing heat providing means, the heat providing section communicating with an inlet end of a reactor section, the reactor section containing catalyst tubes and having an outlet end communicating with a head space section, the catalyst tubes being screened from heat radiation of the heat generating means, the reactor further comprising a recirculation section connecting the head space section to the heat providing section;
   further comprising a feed line and a product line and wherein the reactor section contains reactor panels, each reactor panel comprising a feed header, a product header and adjacent channels, each channel having a length, running from an entrance end to an exit end, and wherein the entrance ends are directly connected to and open into the feed header and the exit ends are directly connected to and open into the product header and wherein the feed header has at least one connection to a feed line and the product header has at least one connection to a product line and wherein part of at least one of the feed header and the product header is detachable giving access to the channel ends.

2. The reactor according to claim 1, wherein the heat providing means comprise at least one burner.

3. The reactor according to claim 1, wherein the entrance end of each catalyst tube is provided with flow restricting means suitable to impose a critical pressure drop on a feed flow entering the tube.

4. The reactor according to claim 1, wherein the product line and the feed line are connected to a heat exchanger to exchange heat between a feed stream and a product stream.

5. The reactor according to claim 1, wherein the reactor panels are located between the inlet end and the outlet end of the reactor section of the reactor.

6. The reactor according to claim 1, further comprising shielding means to prevent direct exposure of the reactor panels to the reactor walls.

7. The reactor according to claim 6, further comprising a temperature control separate from the reactor panels.

* * * * *